(12) United States Patent
Bonanomi et al.

(10) Patent No.: US 11,279,724 B2
(45) Date of Patent: Mar. 22, 2022

(54) EFFICIENT METHOD FOR THE PREPARATION OF CANGRELOR

(71) Applicant: OLON S.P.A., Rodano (IT)

(72) Inventors: Jacopo Bonanomi, Rodano (IT); Mattia Bertolotti, Rodano (IT); Barbara Novo, Rodano (IT)

(73) Assignee: OLON S.P.A., Rodano (IT)

( * ) Notice: Subject to any disclaimer, the term of this patent is extended or adjusted under 35 U.S.C. 154(b) by 135 days.

(21) Appl. No.: 16/762,603

(22) PCT Filed: Oct. 29, 2018

(86) PCT No.: PCT/IB2018/058442
§ 371 (c)(1),
(2) Date: May 8, 2020

(87) PCT Pub. No.: WO2019/092546
PCT Pub. Date: May 16, 2019

(65) Prior Publication Data
US 2021/0179654 A1    Jun. 17, 2021

(30) Foreign Application Priority Data
Nov. 10, 2017 (IT) .................... 102017000128516

(51) Int. Cl.
C07H 1/04 (2006.01)
C07H 19/213 (2006.01)
(52) U.S. Cl.
CPC ............ *C07H 1/04* (2013.01); *C07H 19/213* (2013.01)
(58) Field of Classification Search
None
See application file for complete search history.

(56) References Cited

FOREIGN PATENT DOCUMENTS

| CN | 105 273 026 | 1/2016 |
| WO | WO 94/18216 | 8/1994 |
| WO | WO 2009/066298 | 5/2009 |
| WO | WO 2011/077435 | 6/2011 |

OTHER PUBLICATIONS

International Search Report, PCT/IB2018/058442, dated Feb. 21, 2019.
Ingall A H et al: "Antagonists of the Platelet P2T Receptor: A Novel Approach To Antithromboti C Therapy", Journal of Medicinal Chemistry, American Chemical Society, vol. 42, No. 2, Jan. 1, 1999 (Jan. 1, 1999), pp. 213-220, XP002937224, ISSN: 0022-2623, DOI: 10.1021/JM981072S p. 215, scheme 3.

*Primary Examiner* — Layla D Berry
(74) *Attorney, Agent, or Firm* — Nixon & Vanderhye

(57) ABSTRACT

Disclosed is a process for the preparation of Cangrelor in salt form by preparation and subsequent hydrolysis of an intermediate of formula (IV):

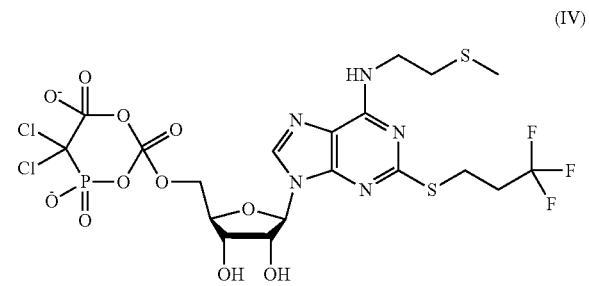

(IV)

The process is characterized by the high yield and purity of the product, and can be used industrially.

20 Claims, No Drawings

EFFICIENT METHOD FOR THE PREPARATION OF CANGRELOR

CONTINUING DATA

This application is a 371 of PCT/IB2018/058442 Oct. 29, 2018

FOREIGN APPLICATIONS

ITALY 102017000128516 Nov. 10, 2017

FIELD OF INVENTION

The present invention relates to a novel process for the synthesis of Cangrelor in the form of a pharmaceutically acceptable salt, in particular tetrasodium salt of high purity. The process is innovative, and is particularly advantageous for application on an industrial scale.

BACKGROUND TO THE INVENTION

Cangrelor tetrasodium is a an ADP $P2Y_{12}$ receptor inhibitor used as an intravenous antiplatelet drug. Many $P2Y_{12}$ inhibitors are used as inhibitors of the platelet activation and aggregation system. Unlike other active ingredients belonging to the same pharmacological class, Cangrelor does not require metabolic conversion to be active.

Cangrelor tetrasodium salt was mentioned for the first time in WO9418216 as a member of an extensive library of nucleotide compounds which have the same mercaptoadenosine structure, but different substituents. The synthesis method disclosed in this patent (Scheme 1) involves initial derivatisation on the thiol of the nitrogenous base of the nucleoside compound of formula (VI) to give the compound of formula (VIII), followed by a second derivatisation on nitrogen, after protecting the hydroxyls as esters, to give the compound of formula (IX). The resulting compound is deprotected in an aqueous alkaline medium to obtain the compound of formula (I) as a crystalline solid. The compound of formula (I) is reacted with phosphorus oxychloride to obtain the intermediate of formula (II), which cannot be, isolated but is converted to the corresponding phosphonic salt of formula (X) by hydrolysis in a basic medium. The compound of formula (X) is purified by ion-exchange chromatography on DOWEX H+ resin, and isolated by freeze-drying the eluted fractions. The compound of formula (X) is then activated by reaction with carbonyldiimidazole (CDI) in the presence of tributylamine to give the compound of formula (XI), which is then reacted with clodronic acid salt (the compound of formula (III)) to obtain Cangrelor as tributylammonium salt. The Cangrelor tributylammonium salt is purified by ion-exchange chromatography on DEAE-SEPHADEX resin, eluting with an aqueous solution of tributylammonium bicarbonate. The Cangrelor tributylammonium salt is then isolated by freeze-drying the eluted fractions. Cangrelor tetrasodium salt is finally obtained by dissolving Cangrelor tributylammonium salt in methanol and precipitating the product by adding sodium iodide in acetone solution.

The main drawback of this synthesis method, apart from the very low overall molar yield (under 10%), is the need for several purifications using chromatography columns on expensive special resins in order to obtain a product of adequate purity. Moreover, the intermediates and the end product are isolated by freeze-drying.

The same patent also discloses a process involving the synthesis of Cangrelor without isolating the intermediate of formula (X). In said process, a solution consisting of tributylamine and clodronic acid salt in triethylphosphate is added to the end-of-reaction mixture in the synthesis step involving formation of the intermediate of formula (X); the resulting mixture is then treated with an aqueous solution of sodium bicarbonate and purified by ion-exchange chromatography (on DEAE-SEPHADEX resin), eluting with an aqueous solution of sodium bicarbonate. Finally, Cangrelor tetrasodium salt (compound V') is obtained by freeze-drying the eluted fractions.

The main drawback of said second process is the use of a large number of moles of clodronic acid to convert the intermediate of formula (X) (about 12 moles per mole of the initial intermediate of formula (X)). In addition, chromatographic purification using an expensive special resin is required to isolate the product. Moreover, said purification may be insufficient to obtain a sufficiently pure product, thus necessitating the use of additional purification techniques. Additionally, the purified fractions must still be freeze-dried in order to isolate Cangrelor tetrasodium. The result is a molar yield which is still fairly low, not exceeding a total of 20%.

Scheme 1

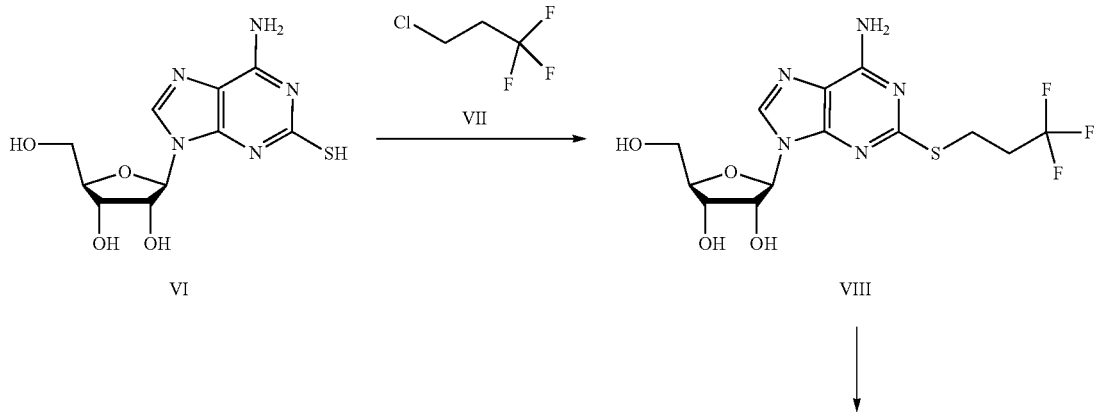

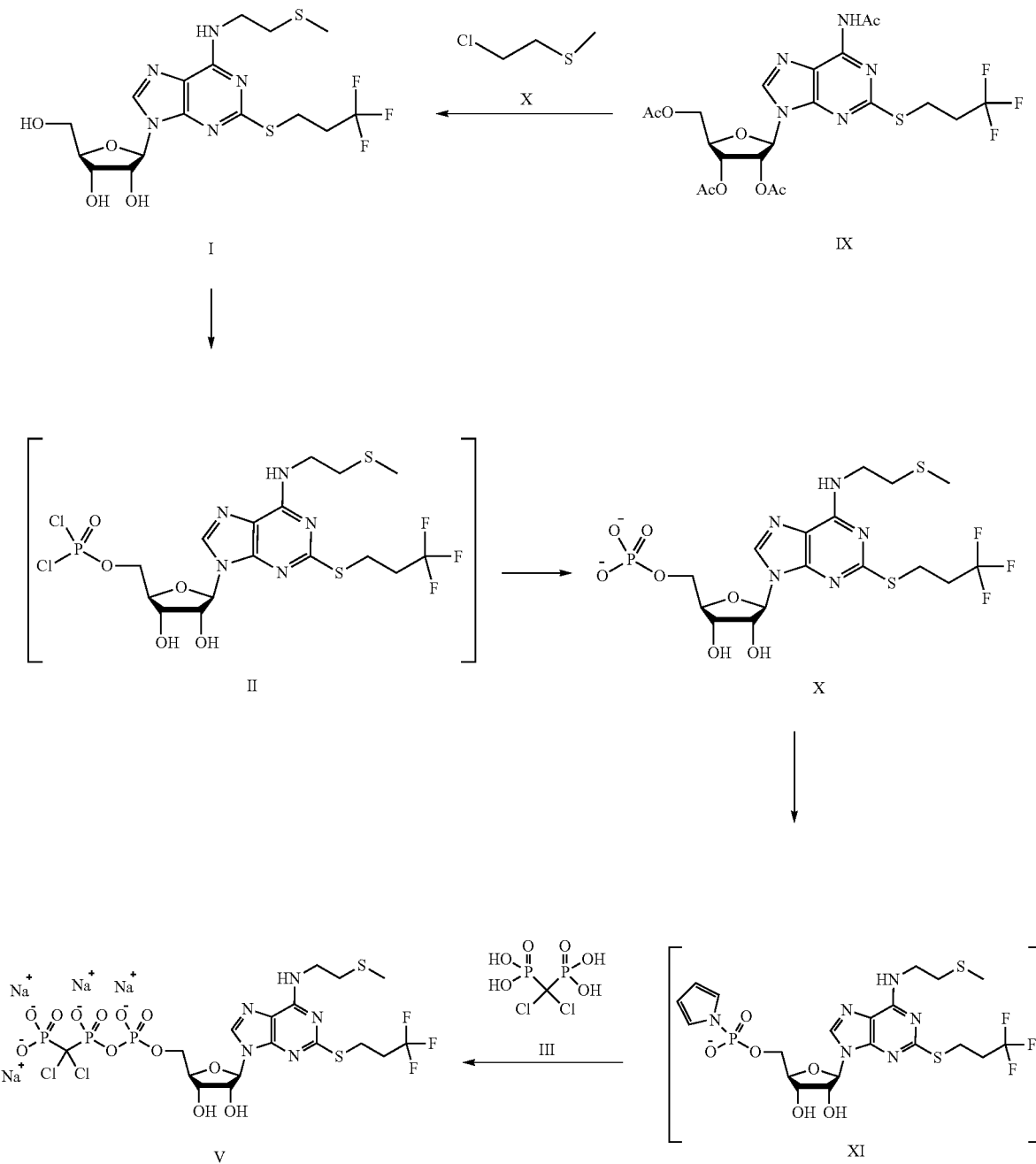

Some recently published Chinese patents, such as CN104447927, CN105273025 and CN105273026, describe a number of improvements to the synthesis of synthetic intermediate I. However, said patents do not relate to the most critical part of the process, i.e. obtaining compound X and the finished Cangrelor.

There is consequently still a need to find an industrially scalable synthesis method that produces Cangrelor tetrasodium salt with a higher yield and purity by limiting the chromatographic purifications and isolation of the products by freeze-drying.

SUMMARY OF THE INVENTION

The present invention relates to a novel process for obtaining Cangrelor in the form of a pharmaceutically acceptable salt, in particular the tetrasodium salt. The process for the preparation of Cangrelor tetrasodium salt of formula (V') is briefly illustrated in Scheme 2. Said process involves synthesis of the intermediate of formula (II), which is directly converted to the cyclic intermediate of formula (IV), optionally isolated and purified by crystallisation. The resulting compound of formula (IV) is then reacted to give Cangrelor directly in the form of tetrasodium salt, which is subsequently purified by affinity chromatography using a polymer resin, and finally isolated by freeze-drying the enriched fractions.

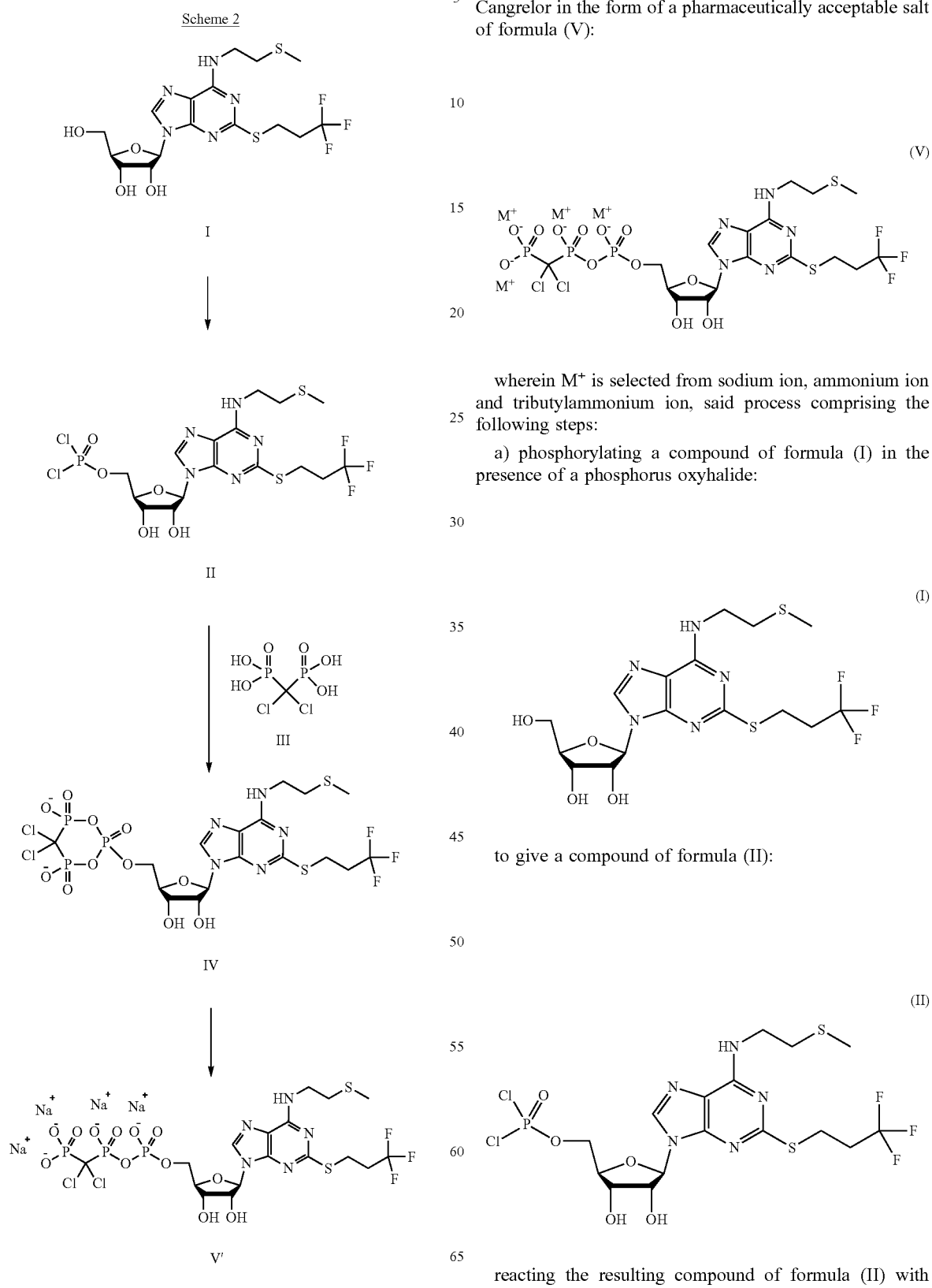

Scheme 2

DETAILED DESCRIPTION OF THE INVENTION

The present invention relates to a process for obtaining Cangrelor in the form of a pharmaceutically acceptable salt of formula (V):

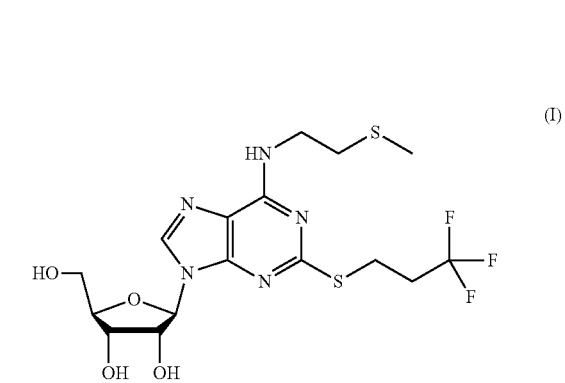

(V)

wherein $M^+$ is selected from sodium ion, ammonium ion and tributylammonium ion, said process comprising the following steps:

a) phosphorylating a compound of formula (I) in the presence of a phosphorus oxyhalide:

(I)

to give a compound of formula (II):

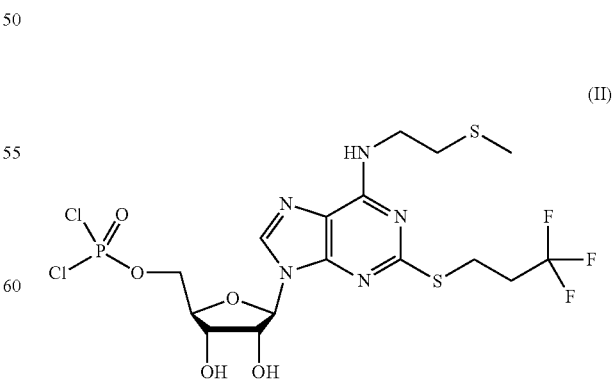

(II)

reacting the resulting compound of formula (II) with clodronic acid to give the compound of formula (IV):

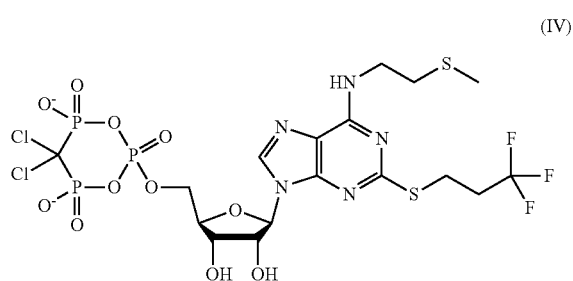

(IV)

c) optionally isolating the resulting compound of formula (IV) by precipitation from the reaction mixture and filtration, and d) converting compound (IV) to Cangrelor in the form of a salt of formula (V) by reacting with water in the presence of a base.

The compound of formula (V) is preferably Cangrelor tetrasodium salt.

Preferably, compound of formula (II) is not isolated, and the reaction of compound of formula (II) with clodronic acid (step b) is effected directly on the reaction mixture obtained in step a).

Cangrelor in salt form is preferably purified by column chromatography and/or crystallisation from a suitable solvent, more preferably by column chromatography and subsequent crystallisation from a suitable solvent.

The phosphorylation of step a) is effected in the presence of a phosphorus oxyhalide such as phosphoryl chloride in a suitable polar aprotic solvent such as tetrahydrofuran, methyltetrahydrofuran, acetonitrile, dichloromethane, trimethyl phosphate and triethyl phosphate or a mixture thereof, preferably tetrahydrofuran, trimethyl phosphate and triethyl phosphate or a mixture thereof, specifically triethyl phosphate and trimethyl phosphate.

The reaction is effected at a temperature ranging from −20° C. to 40° C., preferably from −20° C. to 20° C., for a reaction time ranging from 10 hours to 48 hours, specifically between 15 hours to 24 hours.

The reaction of step b) is effected by adding the reaction mixture obtained in step a) to a clodronic acid solution of formula (III) in the presence of a suitable organic base such as triethyl amine, tributyl amine, di-isopropyl ethyl amine, n-methyl morpholine, N,N-dimethylaniline and dicyclohexyl amine, preferably triethylamine and tributylamine in a suitable solvent such as ethers, esters, alkanes and nitriles, specifically tetrahydrofuran, dioxane, methyl tert-butyl ether, ethyl acetate, cyclohexane, toluene dichloromethane and acetonitrile, preferably tetrahydrofuran, dichloromethane and acetonitrile. The addition is effected by maintaining the two solutions at a temperature ranging from −20° C. to 40° C., preferably from −20° C. to 20° C., and is maintained under stirring for a time ranging from 10 minutes and 180 minutes, preferably from 30 minutes and 120 minutes.

The resulting compound of formula (IV) can be isolated by precipitation (step c) by adding an anti-solvent such as an apolar solvent belonging to the class of ethers or alkanes, such as ethyl ether, isopropyl ether, methyl tert-butyl ether, cyclopentyl methyl ether, n-hexane, cyclohexane and heptane. Compound (IV) is then recovered by filtration of the reaction mixture "as is" or after concentration to a suitable amount of solvent at a temperature ranging from 0° C. to 50° C., specifically between 0° C. to 30° C., to obtain the product as a crystalline solid.

Alternatively, the isolation of compound of formula (IV) can be omitted and the reaction of step d) can be effected directly by adding a basic aqueous solution to the reaction medium to obtain Cangrelor in the form of a salt.

Compound of formula (V) is prepared by reacting intermediate of formula (IV) under basic hydrolysis conditions, in the presence of water and an organic solvent such as ethers, alkanes and nitriles, specifically tetrahydrofuran, dichloromethane, toluene and acetonitrile, or in an aqueous medium only. The reaction is effected in the presence of an organic or inorganic base, specifically ammonia, ammonium carbonate, ammonium bicarbonate, sodium carbonate, sodium bicarbonate, triethylamine, diisopropylamine or tributylamine. The reaction is effected at a temperature ranging from 0° C. to 50° C., specifically between 0° C. to 30° C., and maintained under stirring for a time ranging from 2 hours to 72 hours, preferably from 16 hours to 36 hours.

The product of formula (V) is isolated by chromatography on polymer resin such as HP20SS, eluting with a mixture of water and acetonitrile, followed by freeze-drying. The product thus isolated exhibits high purity.

The product of formula (V) can be purified by crystallisation from a solvent such as acetone, methanol, ethanol or isopropanol or a mixture of one of said substances with water.

The process according to the invention produces Cangrelor in the form of a salt with a high yield and purity. This efficient, novel process avoids the use of large molar amounts of reagents, and allows the synthetic intermediate (cyclic compound IV) to be isolated as a crystalline product. As a result of said improvements, the purification of Cangrelor is less difficult than with the known processes and can be effected with a common polymer resin, using a mixture of water and acetonitrile as eluent phase.

The process of the invention has numerous advantages. They include isolation by crystallisation of cyclic compound (IV), which already has a good level of purity, thereby eliminating high-boiling solvents (which are difficult to remove), excess reagents and the associated by-products from the reaction medium. The end product can then be isolated by fast chromatography with a common polymer resin, by freeze-drying the enriched fractions eluted with water.

Alternatively, the isolation of cyclic compound (IV) can be omitted, and a basic aqueous solution can be added directly to the reaction medium to obtain Cangrelor in the form of a salt which, once again, can be isolated by fast chromatography with a common polymer resin, by freeze-drying the enriched fractions eluted with water.

In both cases the overall yield of the process is much higher than in the processes previously described, and amounts to about 70% molar.

The compound of formula (I) and the reagents used in the process claimed are commercially available.

A further object of the invention is the intermediate of formula (IV).

The invention will now be further illustrated by the following examples.

EXAMPLES

Example 1

Synthesis of Compound of Formula (IV)

Compound I (30.0 g, 0.06 mol) was dissolved in triethyl phosphate (150 mL), and the resulting mixture was cooled to 0° C. Phosphoryl chloride (18.5 g, 0.12 mol) was added in 30 minutes, and the reaction mixture was maintained at 0° C. for 24 hours. The reaction mixture was added in 60 minutes to a mixture of triethyl amine (77.5 g, 0.77 mol) and clodronic acid (27.6 g, 0.06 mol) in dichloromethane (450 mL). The reaction mixture was maintained under stirring at 0° C. for 60 minutes, cyclopentyl methyl ether (300 mL) was then added, and 150 ml of solvent was distilled at low pressure. The resulting suspension was filtered through a Buchner funnel to obtain the compound of formula (IV) as a whitish crystalline solid.

Example 2

Synthesis of Cangrelor Tetrasodium Salt

The compound of formula (IV) obtained in example 1 (30.0 g, 0.02 mol) was suspended in dichloromethane (50 mL). A 10% aqueous solution of NaHCO$_3$ (70 mL) was added to the suspension. The reaction mixture was maintained under stirring at 20° C. for 24 hours. 50 mL of solvent was distilled at low pressure. The resulting solution was loaded onto a chromatography column containing HP20SS resin. The column was eluted using a mixture of water and acetonitrile (95/5) as eluent. The product was isolated by concentrating the enriched fractions at low pressure, and finally crystallised from acetone to obtain Cangrelor as a white crystalline solid (4.8 g, 0.006 mol with over 99% purity (HPLC)).

The invention claimed is:

1. A process for the preparation of cangrelor in the form of a salt of formula (V):

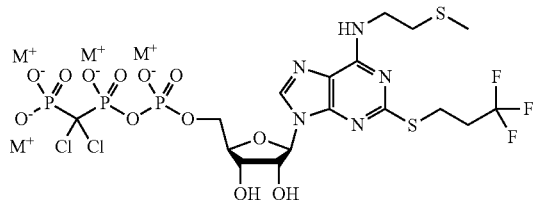

(V)

wherein M$^+$ is selected from sodium ion, ammonium ion and tributylammonium ion,
said process comprising the following steps:
 a) phosphorylating a compound of formula (I) in the presence of phosphorus oxyhalide:

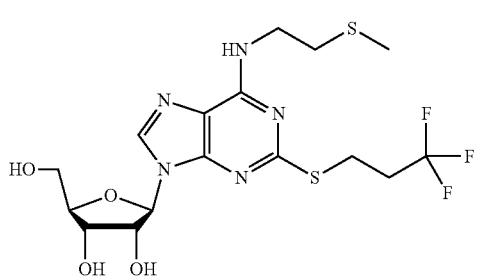

(I)

to give a compound of formula (II):

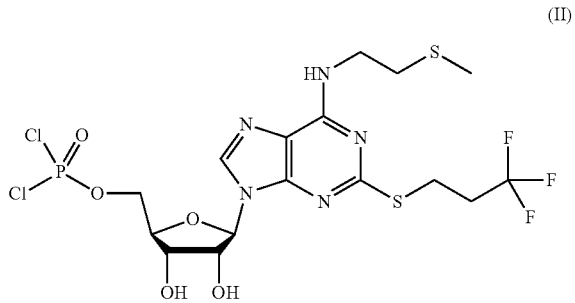

(II)

b) reacting the resulting compound of formula (II) with clodronic acid to give a compound of formula (IV):

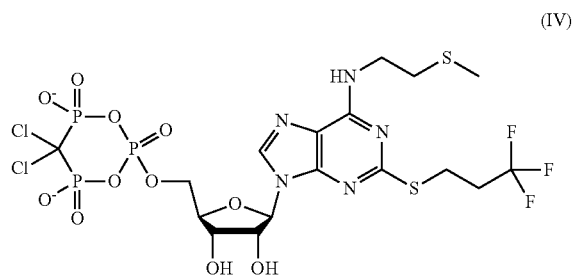

(IV)

c) optionally isolating the resulting compound of formula (IV) by precipitation from the reaction mixture and filtration, and
d) hydrolysing the compound of formula (IV) to give cangrelor in the form of a salt of formula (V) by reaction with water in the presence of a base.

2. The process according to claim 1, wherein the compound of formula (V) is cangrelor tetrasodium salt.

3. The process according to claim 1, wherein the compound of formula (II) is not isolated.

4. The process according to claim 1, wherein the compound of formula (V) in the form of a salt obtained in step d) is purified by column chromatography and/or crystallisation from a suitable solvent.

5. The process according to claim 4, wherein the compound of formula (V) in the form of a salt obtained in step d) is purified by column chromatography and subsequent crystallisation from a suitable solvent.

6. The process according to claim 1, wherein the phosphorus oxyhalide is phosphoryl chloride.

7. The process according to claim 1, wherein the phosphorylation of step a) is carried out in an aprotic polar solvent selected from the group consisting of tetrahydrofuran, methyltetrahydrofuran, acetonitrile, dichloromethane, trimethyl phosphate and triethyl phosphate or a mixture thereof.

8. The process according to claim 1, wherein the phosphorylation of step a) is carried out at a temperature ranging from −20° C. to 40° C.

9. The process according to claim 1, wherein the reaction of step b) is carried out by adding the reaction mixture obtained in step a) to a clodronic acid solution in the presence of an organic base selected from the group con sisting of triethylamine, tributyl amine, di-isopropyl ethyl amine, n-methyl morpholine, N,N-dimethylaniline and dicyclohexylamine.

10. The process according to claim 9, wherein clodronic acid is dissolved in a solvent selected from tetrahydrofuran, dioxane, methyl tert-butyl ether, ethyl acetate, cyclohexane, toluene, dichloromethane and acetonitrile.

11. The process according to claim 9, wherein the addition is carried out maintaining the two solutions at a temperature ranging from −20° C. to 40° C.

12. The process according to claim 1, wherein the precipitation of the compound of formula (IV) in step (c) is obtained by addition of an antisolvent.

13. The process according to claim 1, wherein the compound of formula (IV) obtained in step b) is not isolated.

14. The process according to claim 1, wherein the hydrolysis of step d) is carried out under basic hydrolysis conditions, in the presence of water and an organic solvent, or only in an aqueous medium.

15. The process according to claim 14, wherein the basic hydrolysis is carried out using an organic or inorganic base selected from the group consisting of ammonia, ammonium carbonate, ammonium bicarbonate, sodium carbonate, sodium bicarbonate, triethylamine, diisopropylamine and tributylamine.

16. The compound of formula (IV):

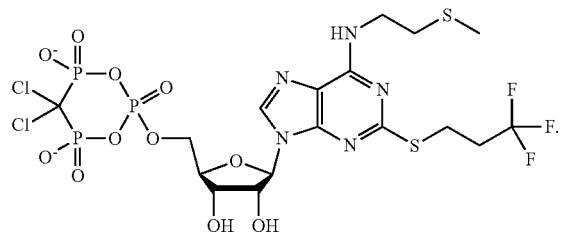

(IV)

17. The process according to claim 2, wherein the compound of formula (II) is not isolated.

18. The process according to claim 2, wherein the compound of formula (V) in the form of a salt obtained in step d) is purified by column chromatography and/or crystallisation from a suitable solvent.

19. The process according to claim 3, wherein the compound of formula (V) in the form of a salt obtained in step d) is purified by column chromatography and/or crystallisation from a suitable solvent.

20. The process according to claim 2, wherein the phosphorus oxyhalide is phosphoryl chloride.

* * * * *